US010107909B2

United States Patent
Taki et al.

(10) Patent No.: US 10,107,909 B2
(45) Date of Patent: Oct. 23, 2018

(54) SUBJECT INFORMATION ACQUISITION APPARATUS, SUBJECT INFORMATION ACQUISITION METHOD, AND PROGRAM

(71) Applicant: CANON KABUSHIKI KAISHA, Tokyo (JP)

(72) Inventors: Hirofumi Taki, Kyoto (JP); Kenichi Nagae, Yokohama (JP); Toru Sato, Kyoto (JP); Junichi Morimoto, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 971 days.

(21) Appl. No.: 14/356,377

(22) PCT Filed: Oct. 22, 2012

(86) PCT No.: PCT/JP2012/077815
§ 371 (c)(1),
(2) Date: May 5, 2014

(87) PCT Pub. No.: WO2013/069486
PCT Pub. Date: May 16, 2013

(65) Prior Publication Data
US 2014/0288431 A1 Sep. 25, 2014

(30) Foreign Application Priority Data

Nov. 7, 2011 (JP) .................................. 2011-243607
Feb. 6, 2012 (JP) .................................. 2012-023343

(51) Int. Cl.
*G01S 15/89* (2006.01)
*A61B 8/06* (2006.01)
*A61B 8/08* (2006.01)

(52) U.S. Cl.
CPC ............ *G01S 15/8984* (2013.01); *A61B 8/06* (2013.01); *A61B 8/488* (2013.01); *G01S 15/8977* (2013.01)

(58) Field of Classification Search
CPC . G01S 15/8984; G01S 15/8977; A61B 8/488; A61B 8/06
See application file for complete search history.

(56) References Cited

U.S. PATENT DOCUMENTS

| 5,000,184 A | 3/1991 | Bonnefous | |
| 6,261,233 B1* | 7/2001 | Kantorovich | ............ A61B 8/06 600/454 |
| 2012/0203113 A1* | 8/2012 | Skerl | .................... A61B 5/0265 600/473 |

FOREIGN PATENT DOCUMENTS

| EP | 541342 A1 | 5/1993 |
| JP | 61-187843 A | 8/1986 |

(Continued)

OTHER PUBLICATIONS

Bonnefous; "Measurement of the complete 3D velocity vector of blood flows"; Oct. 2, 1988; IEEE Ultrasonics Symposium, pp. 795-799 (5 pages).

(Continued)

*Primary Examiner* — Bo J Peng
(74) *Attorney, Agent, or Firm* — Canon USA Inc., IP Division

(57) ABSTRACT

A subject information acquisition apparatus of the present invention includes a transmission/reception unit including a plurality conversion elements which transmit an elastic wave to the subject and receive a reflected wave that is reflected at each position in the subject, a scan line signal acquisition unit which acquires a plurality of signals corresponding to the reflected waves from each position in the subject as scan line signals by using a plurality of reception (Continued)

signals outputted from the conversion elements, and a processing unit which acquires moving information of the object by using the plurality of scan line signals. The processing unit acquires the moving information of the object on the basis of a distribution of cross-correlation values on a plane represented by two axes including an axis of time difference and an axis of distance difference by using a plurality of cross-correlation values between scan line signals at different positions.

21 Claims, 12 Drawing Sheets

(56) References Cited

FOREIGN PATENT DOCUMENTS

| | | |
|---|---|---|
| JP | H02-126175 A | 5/1990 |
| JP | 6-105846 A | 4/1994 |
| JP | 2006-087650 A | 4/2006 |

OTHER PUBLICATIONS

Revised Edition: Handbook of ultrasonic diagnostic equipments, Electronic Industries Association of Japan, Jan. 20, 1997.
Itoh, A., et al., "Restudy of the Techniques and Diagnostic Standards of Breast Diseases Ultrasound Elastography", Sep. 2006, pp. 10-15, MEDIX, vol. 45.

* cited by examiner

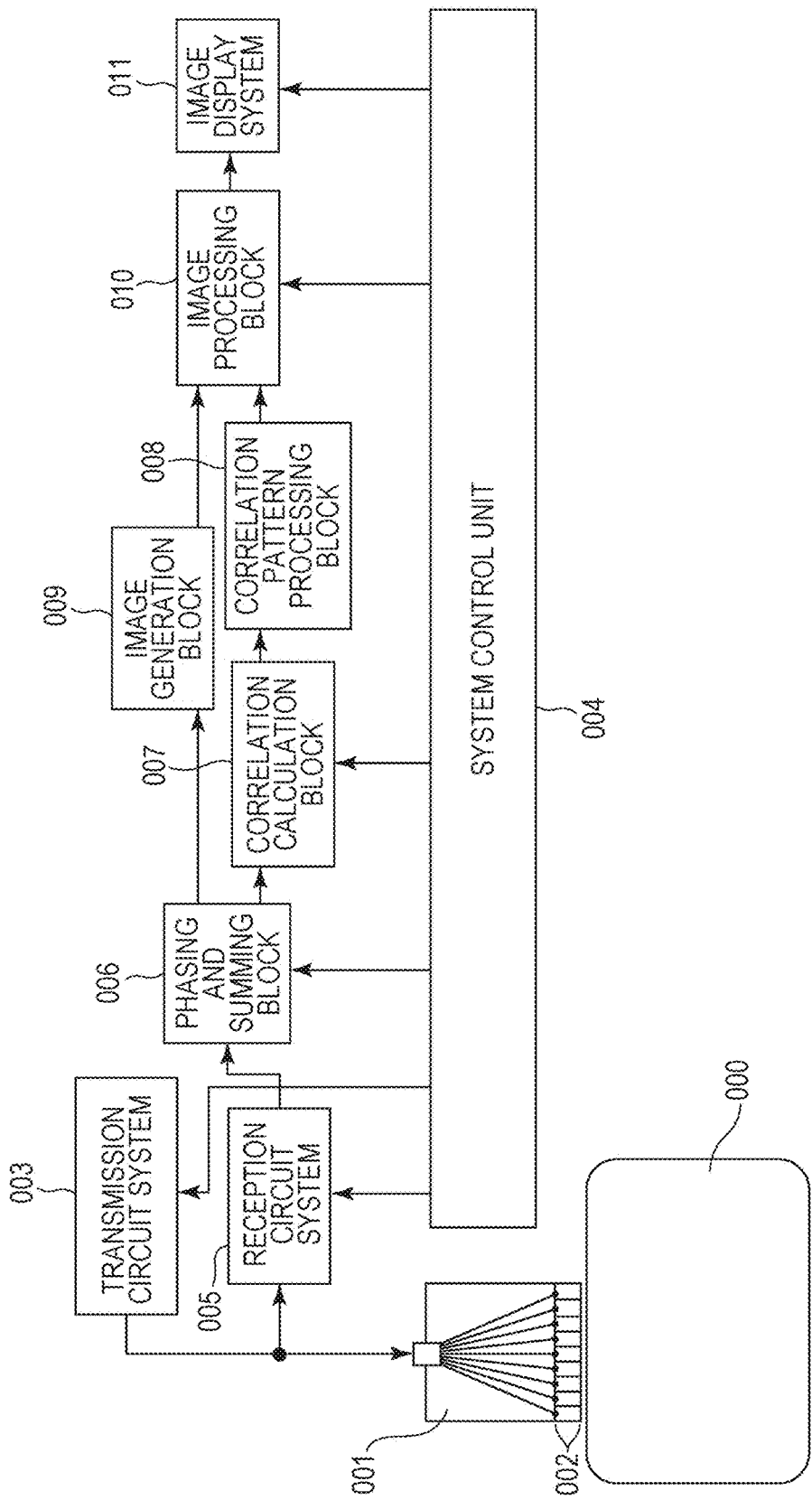

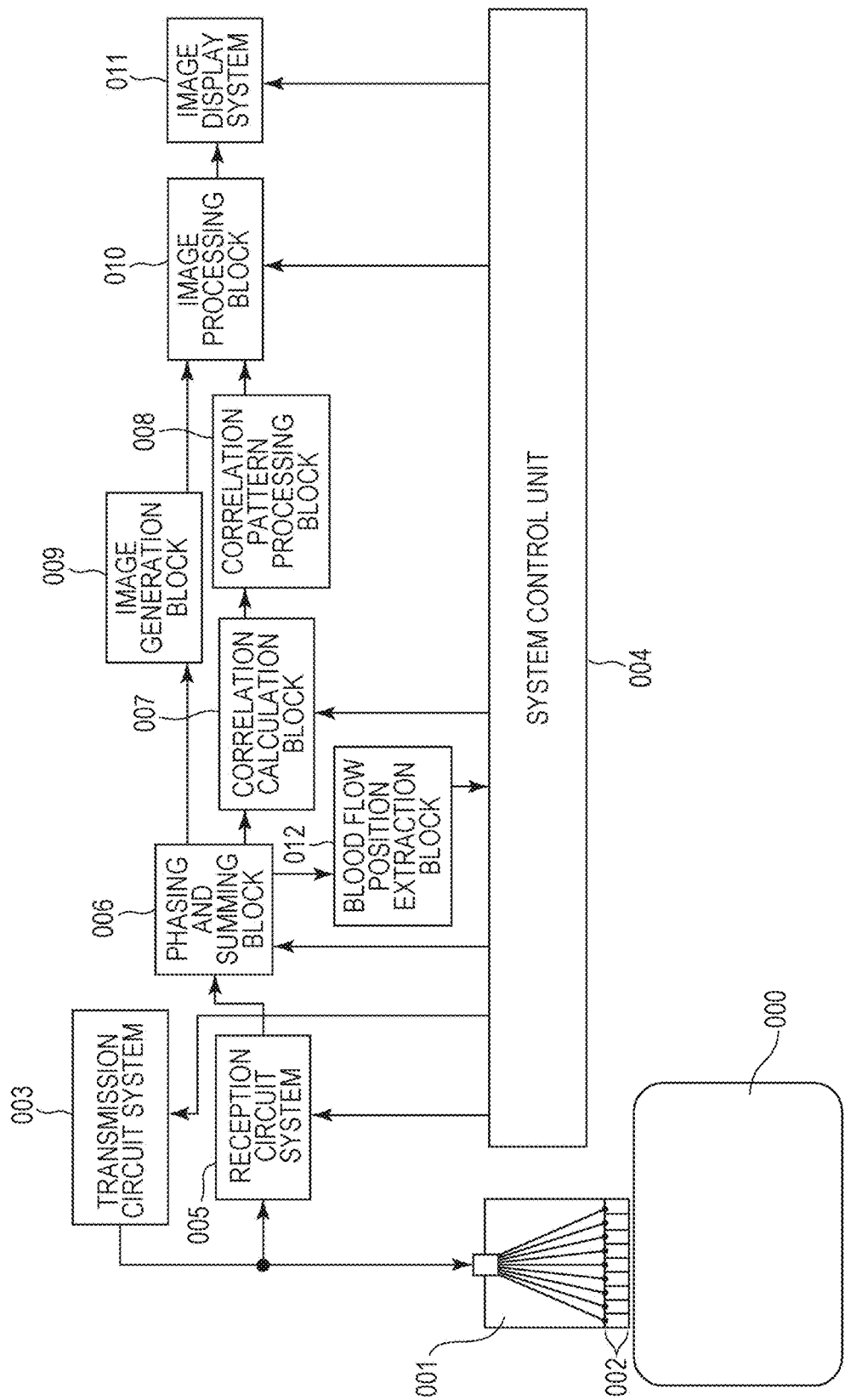

SUBJECT INFORMATION ACQUISITION APPARATUS, SUBJECT INFORMATION ACQUISITION METHOD, AND PROGRAM

TECHNICAL FIELD

The present invention relates to a subject information acquisition apparatus, a subject information acquisition method, and a program, and in particular to a technique for transmitting an elastic wave to a subject, receiving an elastic wave reflected in the subject, and acquiring information in the subject.

BACKGROUND ART

An ultrasonic diagnostic apparatus, which is a subject information acquisition apparatus, is widely used in medical field and the like. The ultrasonic diagnostic apparatus can acquire not only morphological information reflecting an acoustic impedance distribution in a living body, but also moving information of an object such as blood flow velocity information using a Doppler technique.

To acquire the blood flow velocity information, a reflected wave from a region containing blood is used. The reflected wave from a region containing blood is mainly elastic wave (typically, ultrasonic wave) reflected or scattered from red blood cells included in the blood. The wavelength of the ultrasonic wave used by a general ultrasonic diagnostic apparatus is longer than the size of a red blood cell, so that individual red blood cells cannot be distinguished from each other. As a result, the reflected wave from a region containing blood reflects an aspect (shape, orientation, and relative position of individual red blood cells) of an aggregation of scatterers (a scatterer group) formed by a plurality of red blood cells.

To extract blood flow velocity information by using a reflected wave from a scatterer group formed by red blood cells, a technique for obtaining Doppler shift frequency of the reflected wave is often used. However, in principle, the technique for measuring Doppler shift frequency can measure only a projected component in a transmitting/receiving direction (scan line direction) of an ultrasonic beam of the blood flow velocity. In other words, to obtain an original blood flow velocity, it is necessary to perform correction considering an angle between a blood flow direction and an ultrasonic wave transmitting/receiving direction. The correction is a process of dividing a flow velocity estimated from the Doppler shift frequency by the cosine of an angle between the blood flow direction and the ultrasonic wave transmitting/receiving direction. The larger the angle is, the larger the possibility that an error increases.

Therefore, PTL 1 discloses an example that can measure a flow velocity even if the blood flow proceeds in a direction perpendicular to the ultrasonic wave transmitting/receiving direction. The method of PTL 1 acquires a blood flow velocity by calculating a cross-correlation value between two points related to a reflected/scattered waveform of an ultrasonic beam in a tomogram image and dividing a distance between the two points by a time by which the cross-correlation value between the two points reaches a peak.

CITATION LIST

Patent Literature

PTL 1 Japanese Patent Laid-Open No. 61-187843

SUMMARY OF INVENTION

By the way, as the red blood cells in the blood flow in a blood vessel, the distribution of the red blood cells changes. In other words, even when a scatterer group is formed by a plurality of the same red blood cells, the shape, orientation, and relative arrangement of the red blood cells change. By this change, a cross-correlation value (a cross-correlation coefficient) calculated by using reception signals of the reflected signals (reception signals acquired by receiving the reflected signals) acquired at different times decreases as the difference between the times at which the reflected signals are acquired increases.

When such a phenomenon occurs in which the cross-correlation value decreases as the acquisition time difference increases, an error may be generated unless the blood flow velocity information is estimated by taking into account a temporal change of the scatterer group including a relative position change of the scatterer group.

In view of the above problem, the present invention improves acquisition accuracy of moving information of an object by calculating the moving information such as a blood flow velocity by taking into account a temporal change of a scatterer group which is an object in a subject.

A subject information acquisition apparatus of the present invention acquires moving information of an object in a subject and includes a transmission/reception unit including a plurality conversion elements which transmit an elastic wave to the subject and receive a reflected wave that is reflected at each position in the subject, a scan line signal acquisition unit which to acquires a plurality of signals corresponding to the reflected waves from each position in the subject as scan line signals by using a plurality of reception signals outputted from the plurality of conversion elements, and a processing unit which acquires the moving information of the object by using the plurality of scan line signals.

The processing unit acquires the moving information of the object on the basis of a distribution of cross-correlation values on a plane represented by two axes including an axis of time difference and an axis of distance difference by using a plurality of cross-correlation values between scan line signals at different positions.

A subject information acquisition method of the present invention acquires moving information of an object in a subject and includes a step of receiving a plurality of reception signals outputted from a plurality of conversion elements by transmitting an elastic wave to the subject and receiving a reflected wave that is reflected at each position in the subject, a step of acquiring a plurality of signals corresponding to the reflected waves from each position in the subject as scan line signals by using the plurality of reception signals, and a step of acquiring the moving information of the object by using the plurality of scan line signals.

In the step of acquiring the moving information, the moving information of the object is acquired on the basis of a distribution of cross-correlation values on a plane represented by two axes including an axis of time difference and an axis of distance difference by using a plurality of cross-correlation values between scan line signals at different positions.

According to the present invention, it is possible to accurately acquire the moving information of the object by considering the temporal change of the scatterer group, which is the object in the subject.

BRIEF DESCRIPTION OF DRAWINGS

FIG. 1 is a block diagram showing a system overview of a subject information acquisition apparatus according to the present invention.

FIG. 11 is a block diagram showing a system overview of a third embodiment.

DESCRIPTION OF EMBODIMENTS

Figure 2A:
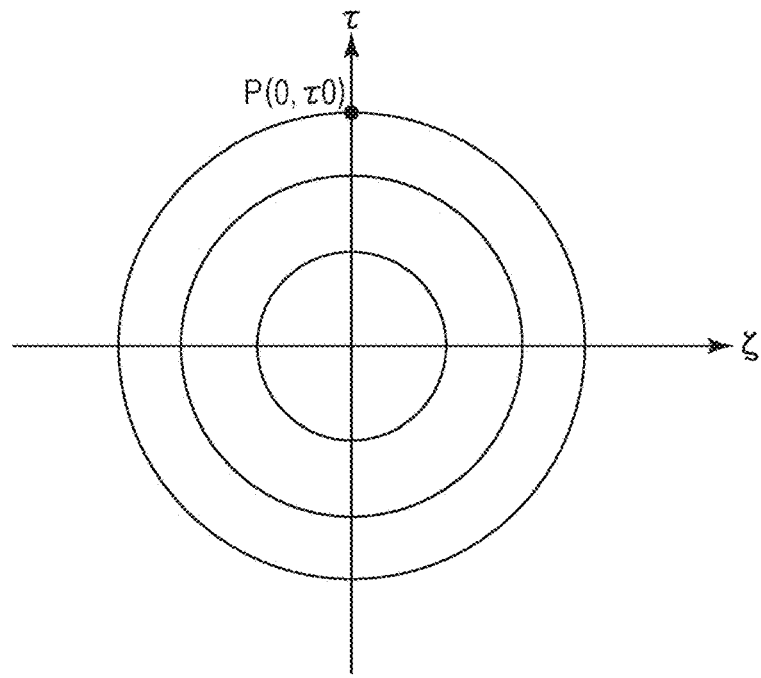
FIGS. 2A and 2B are diagrams showing contour lines of a cross-correlation value.

An embodiment of the present invention will be described with reference to the drawings. In the present invention, an elastic wave is typically an ultrasonic wave and includes an elastic wave called a sound wave, an ultrasonic wave, and an acoustic wave. A subject information acquisition apparatus of the present invention includes an apparatus which transmits an elastic wave to a subject, receives a reflected wave (a reflected elastic wave) reflected in the subject, and acquires subject information as image data. The acquired subject information is information reflecting differences in acoustic impedances in tissue in the subject and moving information of an object in the subject. The moving information of an object in the subject includes velocity information such as blood flow velocity corresponding to moving velocity of a scatterer group formed by red blood cells and velocity distribution of the blood flow and displacement information such as displacement of tissue in the subject and displacement distribution of the tissue.

Basic Configuration of Subject Information Acquisition Apparatus

A configuration of a subject information acquisition apparatus to which the present invention can be applied will be described with reference to FIG. 1. FIG. 1 is a diagram showing a system overview of the subject information acquisition apparatus according to the present invention. The subject information acquisition apparatus according to the present embodiment includes a probe 001, a reception circuit system 005, a transmission circuit system 003, a delay and sum block 006, a correlation calculation block 007, a correlation pattern processing block 008, an image generation block 009, an image processing block 010, a system control unit 004, and an image display system 011. The probe 001 is a transmission/reception unit which transmits an elastic wave to a plurality of positions and receives a reflected wave and which includes a plurality of conversion elements 002 that convert an elastic wave into an electrical signal. The image display system 011 may be provided separately from the subject information acquisition apparatus of the present invention.

In the present invention, the delay and sum block 006, which is a delay and sum unit, is a scan line signal acquisition unit that acquires a plurality of signals at positions in the subject (that is, signals corresponding to elastic waves reflected at the positions) as scan line signals. The correlation calculation block 007, which is a correlation calculation unit, and the correlation pattern processing block 008, which is a correlation processing unit, form at least a processing unit of the present invention.

The transmission circuit system 003, which is a transmission signal generation unit, generates a voltage waveform having a delay time and an amplitude corresponding to a position of interest and a direction of interest as a transmission signal according to a control signal from the system control unit 004. The transmission signal is converted into an elastic wave by the plurality of conversion elements 002 and transmitted into a subject 000 from the probe 001. A reflected wave (elastic wave) reflected in the subject 000 is converted into a plurality of reception signals by the plurality of conversion elements 002. The plurality of reception signals are inputted into the reception circuit system 005, which is a reception signal processing unit.

The reception circuit system 005 amplifies the plurality of reception signals and converts the reception signals into a plurality of digital signals. The plurality of digital signals outputted from the reception circuit system 005 are inputted into the delay and sum block 006. The delay and sum block 006 performs delay processing on the plurality of digital signals and further sums up the digital signals according to a direction and a position to which the elastic wave is transmitted, that is, performs a delay and sum process. The delay and sum process is a process for generating a signal corresponding to a sound pressure of the reflected wave reflected at each position in the subject as a scan line signal. The scan line signal obtained by performing the delay and sum process using a plurality of reception signals in this way is inputted into the correlation calculation block 007 and the image generation block 009.

First, a process in the image generation block 009 will be described. The image generation block 009 calculates an envelope curve of the inputted scan line signals and outputs the envelope curve as an envelope curve signal to the image processing block 010. The envelope curve signal is a signal reflecting a difference in acoustic impedance between each position in the subject. The image generation block 009 may perform various processes as needed, such as applying a bandpass filter to the inputted scan line signal. The image processing block 010 performs an intensity adjustment process and various filter processes on the inputted envelope curve signal and outputs impedance intensity data (so-called B-mode image) to the image display system 011 as distribution information reflecting differences in acoustic impedance in the tissue.

Next, a process in the correlation calculation block 007 will be described. The correlation calculation block 007 calculates a plurality of cross-correlation values (cross-correlation coefficients) between inputted scan line signals according to an instruction from the system control unit 004 and outputs the calculated cross-correlation values to the correlation pattern processing block 008. The correlation pattern processing block 008 calculates moving information such as velocity by using a plurality of inputted cross-correlation values and outputs the moving information to the image processing block 010. The correlation pattern processing block 008 may acquire not only a value of velocity, but also parameters related to the velocity and a velocity distribution indicating velocities at each position as the moving information. The details of the functions of the correlation calculation block 007 and the correlation pattern processing block 008 will be described later with reference to FIGS. 3 to 5.

The image processing block 010 processes the inputted moving information such as velocity and outputs the processed moving information to the image display system 011 as moving information intensity data. The image display system 011 displays the inputted moving information intensity data and the inputted impedance intensity data according to an instruction from the system control unit 004. As a display method, the moving information intensity data and the impedance intensity data may be superimposed together and displayed or may be arranged side by side and displayed. Of course, only the intensity data of each data may be displayed. The display mode can be changed by an instruction from the system control unit 004. The configuration described above is the basic configuration of the subject information acquisition apparatus of the present embodiment.

Behavior of Cross-Correlation Value Considering Temporal Change of Scatterer Group Next, behavior of the cross-correlation value of the reflected wave from a scatterer group will be described before a specific process in the correlation calculation block 007 will be described.

When a scatterer group changes over time (specifically, shapes and orientations of the scatterers and relative positions thereof change over time), a reflected waveform (corresponding to a waveform of a scan line signal) from a scatterer group located at a certain position of interest and a reflected waveform (corresponding to a waveform of a scan line signal) from a scatterer group located at a position of interest $\xi$ away from the certain position of interest are considered. In this case, the larger the $\xi$ is, that is, the larger the distance between the two positions of interest is, the smaller the cross-correlation value between the scan line signal of the certain position of interest and the scan line signal of the position of interest $\xi$ away from the certain position of interest is. When scatters included in a scatter group change an aspect of the scatterer group (change the relative position and the like of the scatterer group), regarding a cross-correlation value between two reflected waves reflected at different times from a scatterer group including the same scatters, the larger the difference $\tau$ between the times, the smaller the cross-correlation value is. In other words, as the distance between the positions of interest increases, or as the difference between the times at which the reflected waves are acquired increases, the cross-correlation value decreases.

FIG. 2A shows a diagram of contour lines of a cross-correlation value in which the horizontal axis represents the distance $\xi$ between the positions of interest and the vertical axis represents the difference $\tau$ between the times at which the reflected waves are acquired. When the scatterer group does not move, the contour lines can be approximated by an elliptical shape (including a circular shape) symmetric to both axes. The cross-correlation value is maximum at a position (the origin) where both axes cross. In other words, the cross-correlation value is maximum when the distance between the positions of interest is 0 and the difference between the times is 0.

Figure 2B:
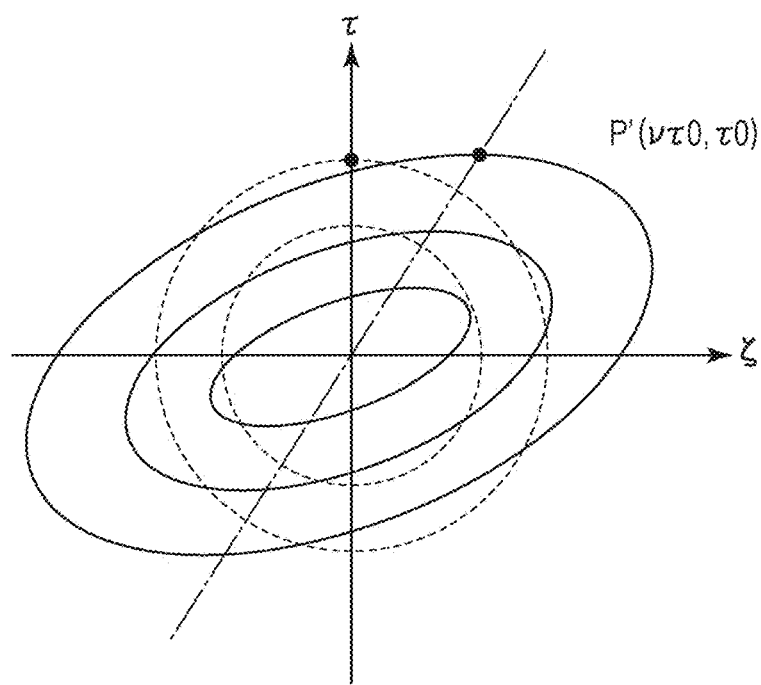

Next, the cross-correlation value in a case where the scatterer group moves at a velocity v is considered. A point P in FIG. 2A (the distance difference between the positions of interest is 0 and the time difference is $\tau 0$) will be considered. The point P moves at the velocity v, so that the point P moves a distance of $v \times \tau 0$ in the time difference $\tau 0$. Specifically, the point P moves to a position of a point P' in FIG. 2B (the distance difference between the positions of interest is $v \tau 0$ and the time difference is $\tau 0$) will be considered. In other words, when the scatterer group moves in the same direction as that of a line connecting P and P', the point P' has the same cross-correlation value as that of the point P. As a result, the contour lines of the cross-correlation value shown in FIG. 2A can be approximated by a distorted elliptical shape as shown in FIG. 2B. At this time, a straight line indicated by a dashed-dotted line in FIG. 2B (line connecting the origin and the point P') is a straight line having a slope of 1/v. Since the slope of the straight line is the reciprocal of the velocity, when the shape approximated by the elliptical shape indicated by solid lines is obtained, the straight line indicated by the dashed-dotted line, that is, the velocity of the scatterer group can be obtained. The straight line indicated by the dashed-dotted line represents a line connecting points at which the cross-correlation value is maximum at each time difference. In other words, the velocity of the scatterer group can be obtained by obtaining information related to the maximum value of the cross-correlation value at a certain time difference (that is, the peak at a certain time difference). The "information related to the maximum value" of the cross-correlation value at a certain time difference may be information that can identify the peak of the cross-correlation value, such as information of the distance difference at which the cross-correlation value is maximum.

In this way, when considering temporal change of the scatterer group itself, the moving information of the scatterer group can be acquired by using the horizontal axis as the distance difference between the positions of interest and the vertical axis as the time difference between times at which the reflected waves are acquired and acquiring distribution of the cross-correlation values on a plane represented by the two axes.

Basic Process Flow

Next, the details of the process of the correlation calculation block 007 and the correlation pattern processing block 008 will be described with reference to FIGS. 3 to 5.

Figure 3:
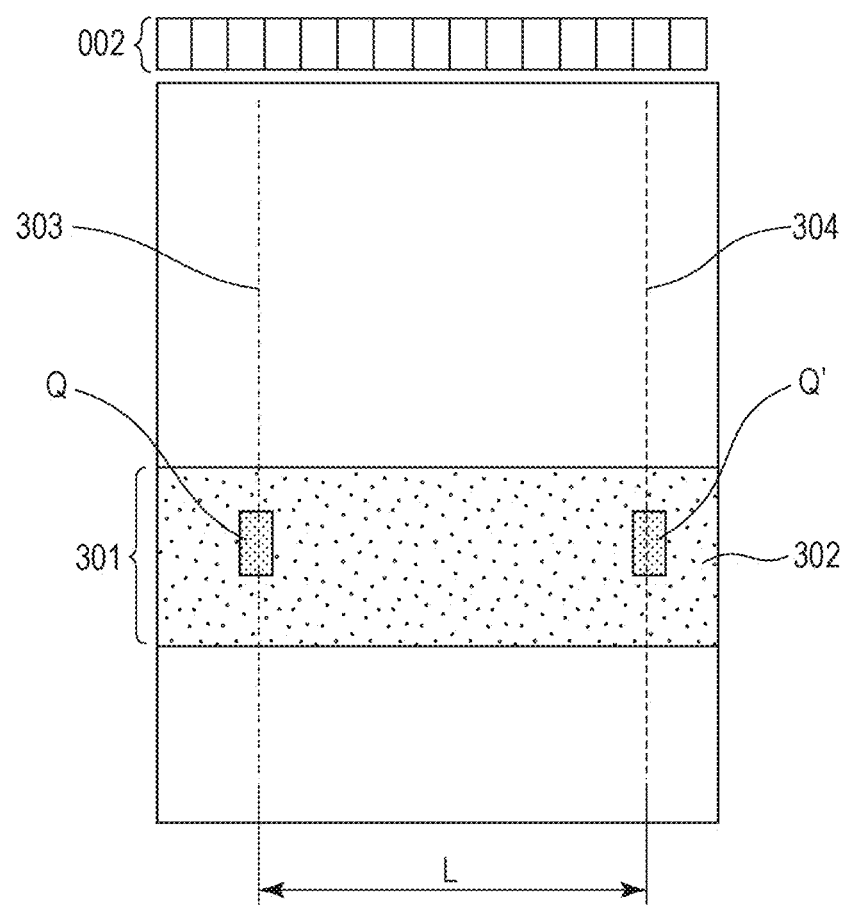
FIG. 3 is a diagram schematically showing a subject and a scatterer group.
Figure 4:
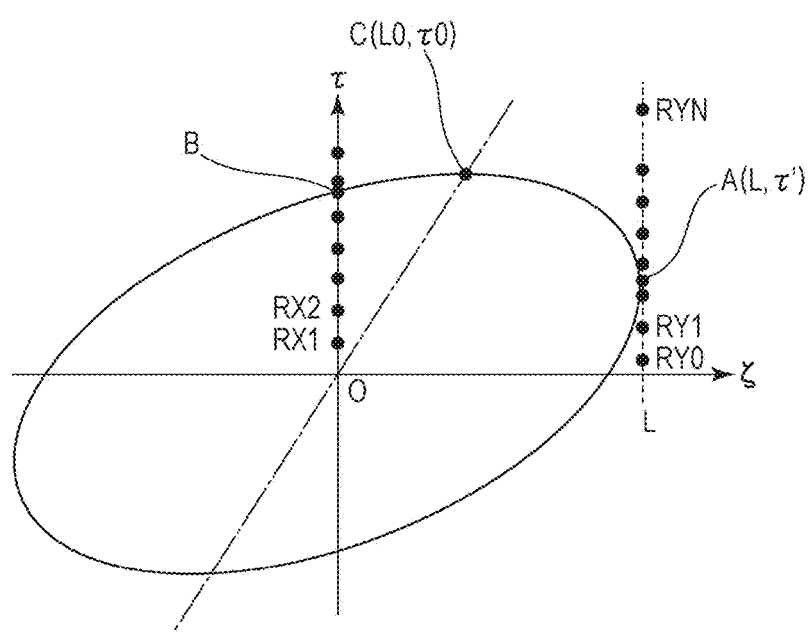
FIG. 4 is a diagram for explaining a concept of a process of the present invention.

FIG. 3 is a diagram schematically showing a scatterer group 302 including red blood cells flowing in a blood vessel 301. FIG. 4 is a diagram for explaining the process of the correlation calculation block 007 and the correlation pattern processing block 008.

Before the process of the correlation calculation block 007 is performed, in the previous delay and sum block 006, the delay and sum process is performed by using a plurality of reception signals obtained when a plurality of conversion elements 002 transmit and receive an elastic wave, and the scan line signal is calculated. In the present embodiment, the delay and sum block 006 calculates a plurality of scan line signals on a scan line 303 and a scan line 304 in FIG. 3. In the present invention, the scan line means a virtual line formed in a traveling direction of an elastic wave transmitted from the probe and the scan line signal means a signal at a certain position on the scan line. In other words, one scan line is a virtual line formed by arranging the scan line signals in the traveling direction of the elastic wave.

Figure 5:
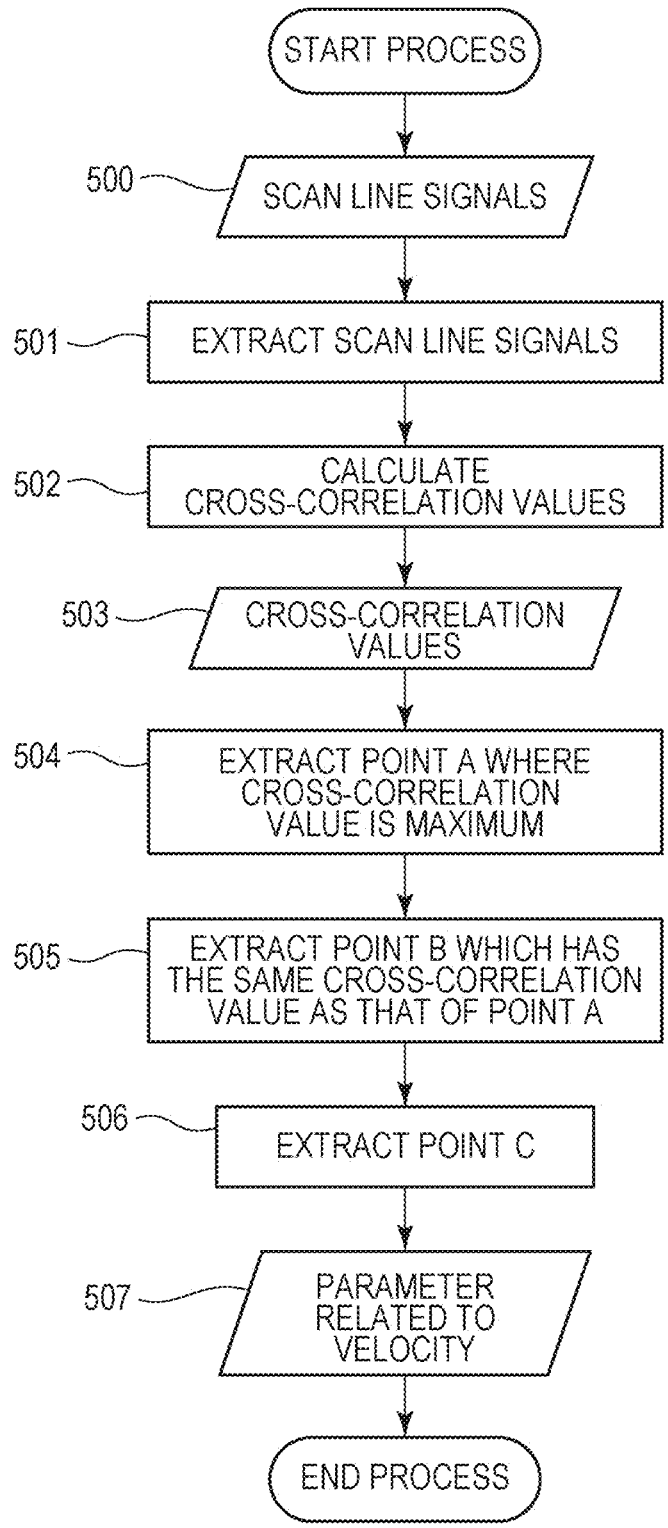
FIG. 5 is a flowchart showing processing steps according to the present invention.

FIG. 5 is a flowchart showing a process flow in the correlation calculation block 007 and the correlation pattern processing block 008. First, in step 500, the scan line signals on the scan line 303 and the scan line 304 calculated by the delay and sum block 006 are inputted into the correlation calculation block 007.

In step 501, the correlation calculation block 007 extracts a scan line signal X0 using a reception signal (a reception signal acquired when a reflected signal is received) of a reflected signal from a region Q on the scan line 303 and a scan line signal Y0 using a reception signal of a reflected signal from a region Q' on the scan line 304. In short, the correlation calculation block 007 extracts the scan line signal X0 of the region Q and the scan line signal Y0 of the region Q'. The distance between the region Q and the region Q' is L. Thereafter, the elastic wave is transmitted and received a plurality of times and the scan line signals X1, X2, X3, X4, . . . , and XN of the region Q and the scan line signals Y0, Y1, Y2, Y3, Y4, . . . , and YN of the region Q' are extracted (N is a positive integer).

In step 502, the correlation calculation block 007 calculates a cross-correlation value R ($\xi$, $\tau$) between the scan line signals by using the formula below and outputs the cross-correlation value R ($\xi$, $\tau$). Here, for example, the correlation calculation block 007 calculates cross-correlation values between the scan line signal X0 and the other scan line signals (X1, X2, X3, . . . , and XN and Y0, Y1, Y2, . . . , and YN).

$$R(\xi, \tau) \max_u \frac{\sum_{t'=0}^{T} S(x_1, t_1+t')S(x_2, t_2+t'+u)}{\sqrt{\sum_{t=t_1}^{t_1+T} |S(x_1, t)|^2 \sum_{t=t_2}^{t_2+T} |S(x_2, t+u)|^2}}$$ [Formula 1]

In the formula, S(x, t) is a scan line signal on an acquisition position x and an acquisition time t. In the formula, $\xi$=x2−x1, and $\tau$=t2−t1. In the formula, u is used to adjust an extraction position of the scan line signal used to calculate the cross-correlation value. The cross-correlation value can be more stably calculated by searching the maximum value in a time width corresponding to a wavelength.

In step 503, a plurality of cross-correlation values outputted from the correlation calculation block 007 are inputted into the correlation pattern processing block 008. The correlation pattern processing block 008 estimates moving information between the region Q and the region Q' by using cross-correlation values between the scan line signal X0 and the other scan line signals.

Hereinafter, an example of a process of the correlation pattern processing block 008 will be described with reference to FIG. 4. The horizontal axis in FIG. 4 indicates a distance difference between the two positions of interest (region Q and region Q'). The vertical axis indicates time differences from when the scan line signal X0 is acquired to when the other scan line signals are acquired (that is, differences between the acquisition time of the reflected wave indicated by the scan line signal X0 and the acquisition times of the reflected waves indicated by the other scan line signals). Points RX1, RX, RX3, . . . , and RXN and RY0, RY1, RY2, . . . , and RYN are points at which calculated cross-correlation values are plotted on coordinate axes on a plane including the two axes. For example, the point RY0 is a point at which the cross-correlation value between the scan line signal X0 and the scan line signal Y0 is plotted at a position where the horizontal axis indicates the distance (L) between the region Q and the region Q' and the vertical axis indicates the time difference between a time when the scan line signal X0 is acquired and a time when the scan line signal Y0 is acquired. The points RX1, RX, RX3, . . . , and RXN are points at which the cross-correlation values between the scan line signals on the same region Q are plotted for each acquisition time difference.

Next, in step 504, the correlation pattern processing block 008 extracts a point A (L, $\tau'$) at which the cross-correlation value is maximum in a region from the point RY0 to the point RYN. In this case, instead of the cross-correlation values of the points RY0 to RYN, a point at which the cross-correlation value is maximum may be more accurately extracted by interpolating between the cross-correlation values.

In step 505, a point B is extracted, which has the same cross-correlation value as that of the point A, in a region from the point RX0 to the point RXN. In the same manner as in step 504, the point B may be more accurately obtained by interpolating between the cross-correlation values from the point RX1 to the point RXN. A distorted elliptical shape acquired in this way, which has a tangent line (formed by the points RY0 to RYN) at the point A and which passes through the point B, approximates the contour line of the cross-correlation value.

Further, in step 506, a point C (L0, $\tau$0) is obtained at which a maximum value in the vertical axis direction appears on the distorted elliptical shape. The reciprocal (L0/$\tau$0) of the slope of a straight line passing through the point C and the origin O is the velocity at which the scatterer group passes between the region Q and the region Q'.

In step 507, the correlation pattern processing block 008 outputs a parameter related the velocity obtained in this way to the image processing block 010 as the moving information. In this way, the correlation pattern processing block 008 can acquire the moving information between the region Q and the region Q' by using a plurality of cross-correlation values between the scan line signal X0 and the other scan line signals.

Here, a case is considered in which the velocity is estimated by using only cross-correlation values acquired simply using the region Q and the region Q' without considering the temporal change of the scatterer group. In this case, it is assumed that a point at which the maximum value of the cross-correlation values between the scan line signal X0 and the scan line signals Y0 to YN acquired in the region Q' appears, that is, a position near the point A, is a time point at which the scatterer group passes. In this case, the calculated velocity is L/$\tau'$, which is different from the true value (L0/$\tau$0). It is understood that the present invention can improve the accuracy of calculating the velocity by considering the temporal change of the scatterer group.

In this way, when calculating the moving information by using at least cross-correlation values acquired at a plurality of different positions, a distribution of the cross-correlation values in a plane represented by two axes including the time difference axis and the distance difference axis is acquired, so that the accuracy of the calculation can be improved. In short, in the present invention, the distribution of the cross-correlation values on the aforementioned plane is acquired, so that information related to the maximum value of the cross-correlation values at a certain time difference can be obtained, and thus more accurate moving information can be obtained.

Here, two positions of interest, that is, region Q and region Q', are used. However, the positions of interest are not limited to those regions (see the first to the third embodiments). By considering more points, it is possible to acquire a velocity distribution in a two-dimensional plane or a three-dimensional space as the moving information. It is also possible to acquire a velocity distribution in a two-dimensional plane or a three-dimensional space by using a velocity obtained by the Doppler method in the scan line direction and by calculating a velocity using the method of the present invention in a direction other than the scan line direction (for example, a direction perpendicular to the scan line direction). In other words, it is possible to acquire the moving information such as the velocity distribution by combining the method of the present invention and the Doppler method.

Further, although an example where the scan line signals of the region Q and the region Q' are acquired at different timings is described here, the present invention can be applied to a case in which the elastic wave is transmitted to both regions at the same time and both regions are acquired at the same timing.

Hereinafter, embodiments of the subject information acquisition apparatus according to the present invention will be described in detail with reference to the drawings.

First Embodiment

A first embodiment of the present invention will be described with reference to FIGS. 1, 5, 6, and 7. In the present embodiment, an example will be described in which a velocity of a scatterer group is obtained when performing a control such as linear electronic scanning where a position for transmitting and receiving an elastic wave beam (ultrasonic pulse) is sequentially moved (that is, the position for receiving the scan line signal is sequentially moved) in a range where the subject information is acquired. In the present embodiment, electronic scanning for sequentially transmitting an elastic wave beam to a plurality of positions is performed twice or more.

Figure 6:
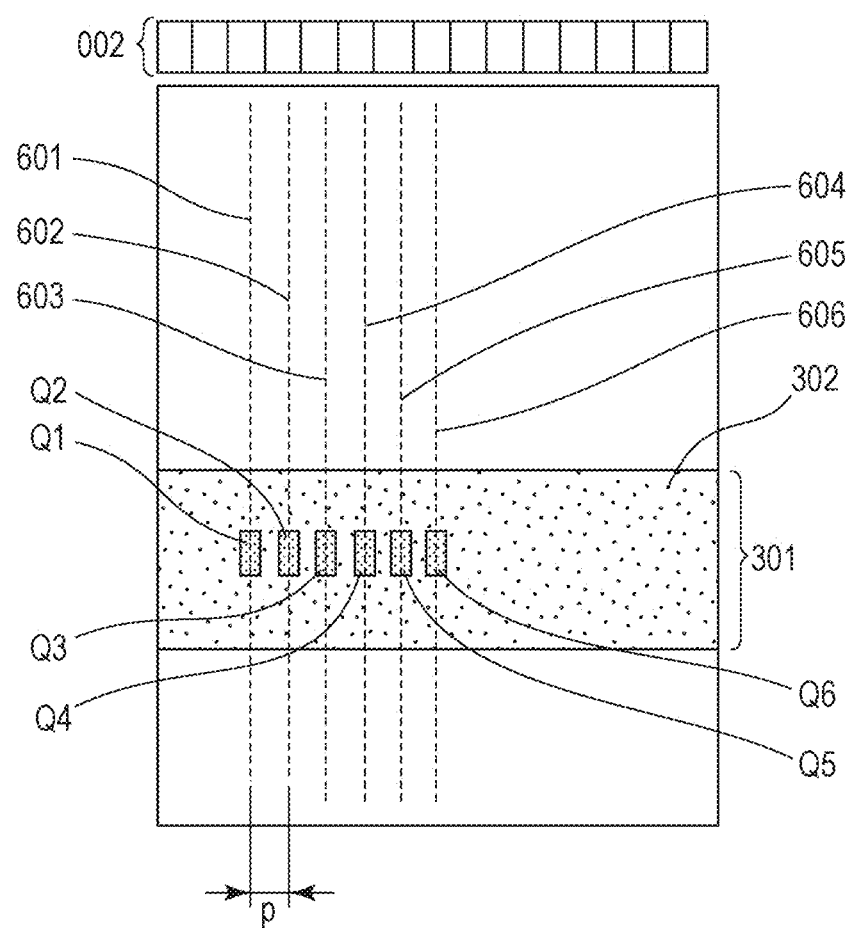
FIG. 6 is a diagram schematically showing a subject and a scatterer group.
Figure 7:
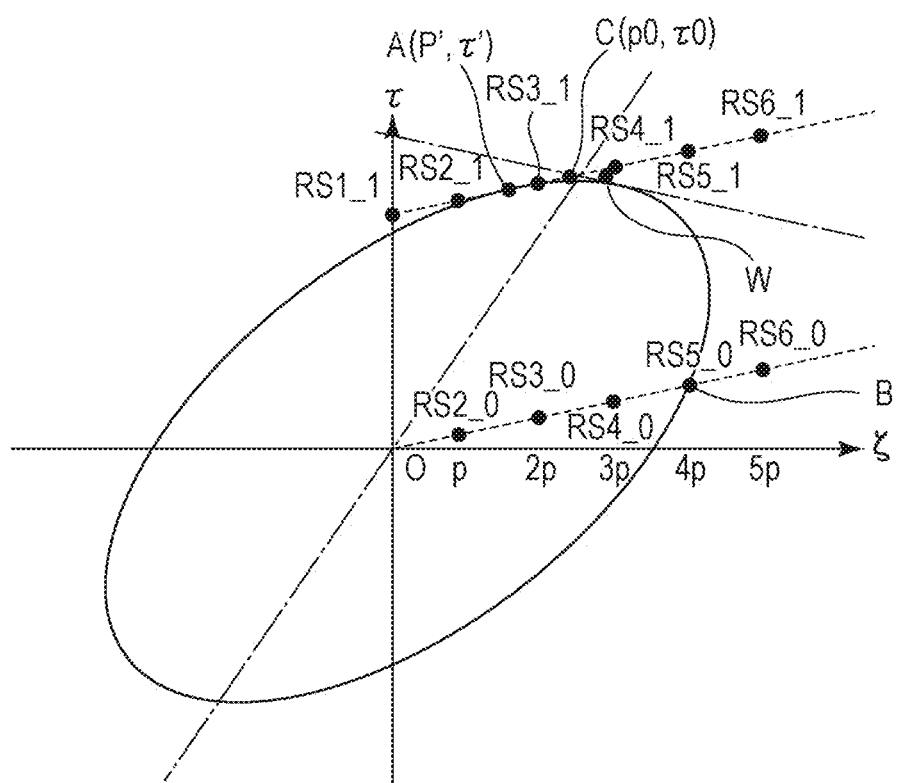
FIG. 7 is a diagram for explaining a concept of a first embodiment.

An apparatus configuration of the subject information acquisition apparatus of the present embodiment is the same as that described using FIG. 1, so that the description of the components will be omitted and only process content of the correlation calculation block 007 and the correlation pattern processing block 008, which is different from that described above, will be described. The process of the correlation calculation block 007 and the correlation pattern processing block 008 of the present embodiment is basically the same as that shown in the flow described using FIG. 5, so that only process content of each step, which is different from that described above, will be described in detail. FIG. 6 is a diagram schematically showing a scatterer group 302 including red blood cells flowing in a blood vessel 301. FIG. 7 is a diagram for explaining concept of the process of the correlation calculation block 007 and the correlation pattern processing block 008.

Process Flow of the First Embodiment

Before the process of the correlation calculation block 007 is performed, in the previous delay and sum block 006, the delay and sum process is performed by using a plurality of reception signals obtained when a plurality of conversion elements 002 transmit and receive an elastic wave, and a plurality of scan line signals on scan lines 601 to 606 are calculated. Here, a plurality of scan line signals are acquired by two or more electronic scanning operations. In step 500, these scan line signals are inputted into the correlation calculation block 007.

In step 501, the scan line signals described below are extracted from a plurality of inputted scan line signals as scan line signals obtained by the first electronic scanning. The regions below are away from each other by a distance p.

Scan line signal S1_0 using a reception signal of a reflected signal from a region Q1 on the scan line 601, Scan line signal S2_0 using a reception signal of a reflected signal from a region Q2 on the scan line 602, Scan line signal S3_0 using a reception signal of a reflected signal from a region Q3 on the scan line 603, Scan line signal S4_0 using a reception signal of a reflected signal from a region Q4 on the scan line 604, Scan line signal S5_0 using a reception signal of a reflected signal from a region Q5 on the scan line 605, and Scan line signal S6_0 using a reception signal of a reflected signal from a region Q6 on the scan line 606.

Thereafter, transmission and reception are repeatedly performed, and further, the following scan line signals are extracted as scan line signals obtained by the second electronic scanning.

Scan line signal S1_1 using a reception signal of a reflected signal from a region Q1, Scan line signal S2_1 using a reception signal of a reflected signal from a region Q2, Scan line signal S3_1 using a reception signal of a reflected signal from a region Q3, Scan line signal S4_1 using a reception signal of a reflected signal from a region Q4, Scan line signal S5_1 using a reception signal of a reflected signal from a region Q5, and Scan line signal S6_1 using a reception signal of a reflected signal from a region Q6.

Although the scan line signals obtained by the second electronic scanning are shown here, the scan line signals obtained by the third electronic scanning may be extracted. In other words, the scan line signals obtained by the second and the following electronic scanning may be extracted.

In step 502, the correlation calculation block 007 calculates the cross-correlation values between these scan line signals and outputs the calculated cross-correlation values. Here, for example, the correlation calculation block 007 calculates the cross-correlation values between the scan line signal S1_0 and the other scan line signals (S1_1, S2_0, S2_1, S3_0, S3_1, S4_0, S4_1, S5_0, S5_1, S6_0, and S6_1). Here, the scan line signal S1_0 represents a scan line signal at a predetermined datum point among the scan line signals obtained by the first electronic scanning. In other words, in the present embodiment, the region Q1, which is the first transmission position, is defined as the datum point. However, in the present invention, the datum point is not limited to the first transmission position, and a position other than the region Q1 (for example, the region Q3) may be defined as the datum point. For example, if the region Q3 is defined as the datum point, the cross-correlation values between the scan line signal S3_0 and the other scan line signals may be calculated.

In step 503, the cross-correlation values outputted from the correlation calculation block 007 are inputted into the correlation pattern processing block 008. The correlation pattern processing block 008 estimates the moving information in a region from the region Q1 to the region Q5 by using the cross-correlation values between the scan line signal S1_0 (the scan line signal at the datum point in the first electronic scanning) and the other scan line signals (scan line signals other than the scan line signal S1_0).

Hereinafter, an example of the process of the correlation pattern processing block 008 will be described with reference to FIG. 7. The horizontal axis in FIG. 7 indicates distance differences between the region Q1 and the regions Q2, Q3, Q4, Q5, and Q6). The vertical axis indicates time differences between when the scan line signal S1_0 is acquired and when the other scan line signals are acquired (that is, differences between the acquisition time of the reflected wave indicated by the scan line signal S1_0 and the acquisition times of the reflected waves indicated by the other scan line signals). Points RS2_0, RS3_0, . . . , and RS6_0, and RS1_1, RS2_1, . . . , and RS6_1 in FIG. 7 are points at which calculated cross-correlation values are plotted on coordinate axes on a plane including the two axes.

For example, the point RS2_1 is a point at which the cross-correlation value between the scan line signal S1_0 and the scan line signal S2_1 is plotted at a position where the horizontal axis indicates the distance p between the region Q1 and the region Q2 and the vertical axis indicates the acquisition time difference between the scan line signal S1_0 and the scan line signal S2_1.

Next, in step 504, a point A (p', τ') is extracted at which the cross-correlation value is maximum in a region from the point RS1_1 to the point RS6_1. In this case, instead of the cross-correlation values of each point, a point at which the cross-correlation value is maximum may be more accurately extracted by interpolating between the cross-correlation values.

In step 505, a point B is extracted, which has the same cross-correlation value as that of the point A, in a region from the point RS2_0 to the point RS6_0. In the same manner as in step 504, the point B may be more accurately obtained by interpolating between the cross-correlation values of these points. A distorted elliptical shape acquired in this way, which has a tangent line (formed by the points RS1_1 to RS6_1) at the point A and which passes through the point B, approximates the contour line of the cross-correlation value.

Further, in step 506, a point C (p0, τ0) is obtained at which a maximum value in the vertical axis direction appears on the distorted elliptical shape. The reciprocal (p0/τ0) of the slope of a straight line passing through the point C and the origin O is the velocity at which the scatterer group passes between the regions. As described above, the straight line represents a line where the maximum values of the cross-correlation value at each time difference are connected.

Here, a case is considered in which the velocity is estimated by using only cross-correlation values, which are simply acquired, without considering the temporal change of the scatterer group. In this case, it is assumed that a point at which the maximum value of the cross-correlation values between the scan line signal S1_0 and the scan line signals RS1_1 to RS6_1 appears, that is, a position near the point A, is a time point at which the scatterer group passes. In this case, the calculated velocity is p'/τ', which is different from the true value (p0/τ0). It is understood that the present embodiment can improve the accuracy of estimating the velocity by considering the temporal change of the scatterer group. Specifically, the distribution of the cross-correlation values on the plane represented by two axes including the axis of time difference and the axis of distance difference is acquired, so that information related to the maximum value of the cross-correlation values at a certain time difference can be obtained, and thus more accurate moving information can be obtained.

Finally, in step 507, the correlation pattern processing block 008 outputs a parameter related the velocity obtained by the steps described above to the image processing block 010 as the moving information. In this way, the correlation pattern processing block 008 can acquire the moving information of the scatterer group by using the cross-correlation values between the scan line signal S1_0 and the other scan line signals. The correlation pattern processing block 008 may acquire not only the parameter related to the velocity, but also the moving information as the velocity distribution that indicates velocities at each position.

Figure 8:
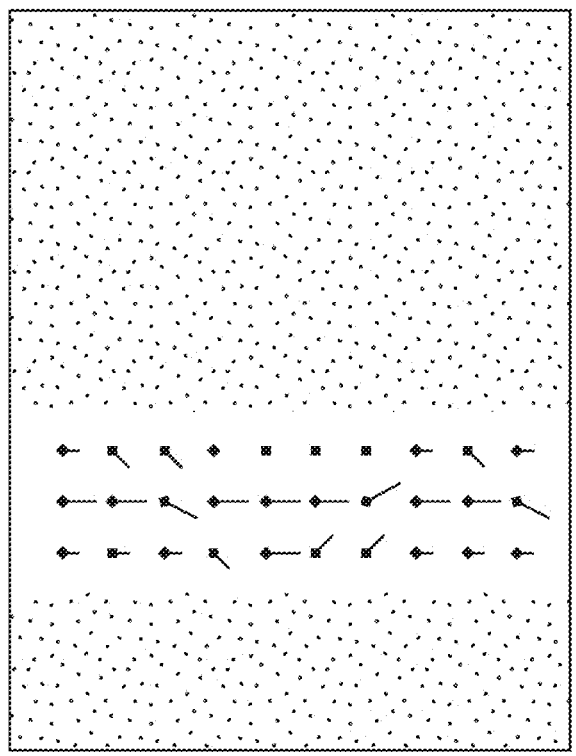
FIG. 8 is a schematic diagram of an example of a display of the first embodiment.

The moving information such as the parameter related to the velocity and the velocity distribution that are finally obtained is image-processed by the image processing block 010 to be displayed and displayed by the image display system 011. FIG. 8 is a schematic diagram showing an example of the display. FIG. 8 shows the magnitude of the velocity by the length of a line segment from a measuring point and the direction of the velocity (the direction in which the scatterer group flows) by the direction of the line segment by using the obtained velocity distribution. Although a line segment is used to display the velocity in FIG. 8, arrows may also be used and the magnitude of the velocity can be represented by brightness, color, thickness, or the like. Further, the direction of the velocity may be represented by a color. Further, the velocity may be represented by a flow line by using the velocity distribution. Not only by arranging the positions of interest in the horizontal direction as in the present embodiment, but also by using a larger number of points, it is possible to calculate a velocity distribution in a two-dimensional plane and a three-dimensional space.

Further, in the present embodiment, the scan line signal is acquired by sequentially moving the position at which the elastic wave is transmitted and received (that is, while moving the scan line by electronic scanning), so that it is possible to obtain the velocity distribution while acquiring a normal B-mode image. The accuracy can be further improved by also using data acquired by reversing the direction in which the scan line is moved.

Further, the calculation accuracy of the velocity distribution can be improved by setting the direction in which the scan line is moved so that the direction intersects the direction in which the scatterer group moves (typically, the direction is set to be opposite to the direction in which the scatterer group moves). Therefore, after detecting the moving direction of the scatterer group in the subject, a control may be performed to move the scan line in a direction opposite to the moving direction.

Here, the reason why the calculation accuracy of the velocity distribution is improved by the above method will be described with reference to FIG. 7. When the moving direction of the scan line is set to be opposite to the direction in which the scatterer group moves and the cross-correlation value on the straight line indicated by the dashed-dotted line in FIG. 7 is calculated, the cross-correlation value is maximum at the point W on the dashed-dotted line and the point W is a tangent point on the distorted ellipse. The point A in FIG. 7 is a point where the moving direction of the scan line is set the direction in which the scatterer group moves and the cross-correlation value on a straight line indicated by a dotted line in FIG. 7 is maximum (that is, the point A is a tangent point on the ellipse). Here, as understood from FIG. 7, when comparing the curvatures of the ellipse at the positions of the points A and W, the curvature at the point W is larger than that at the point A, and the cross-correlation value changes more largely on the tangent line including the point W than on the tangent line including the point A. Therefore, when obtaining a point where the cross-correlation value is maximum on a straight line, it is highly probable that the point can be more accurately obtained on the tangent line including the point W than on the tangent line including the point A. Therefore, the scan line is moved in a direction intersecting the moving direction of the scatterer group (typically, in a direction opposite to the moving direction of the scatterer group), so that, as a result, it can be expected that the calculation accuracy of the velocity distribution is improved.

Second Embodiment

Figure 9A:
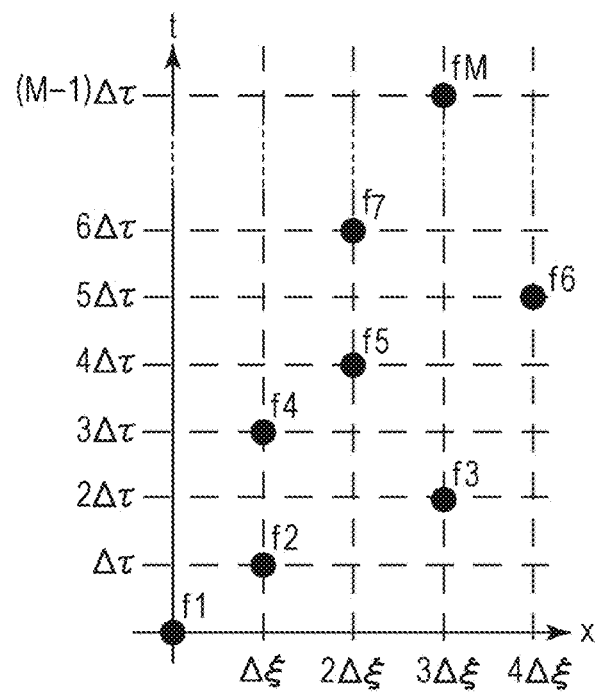
FIGS. 9A and 9B are diagrams for explaining a concept of a second embodiment.
Figure 9B:
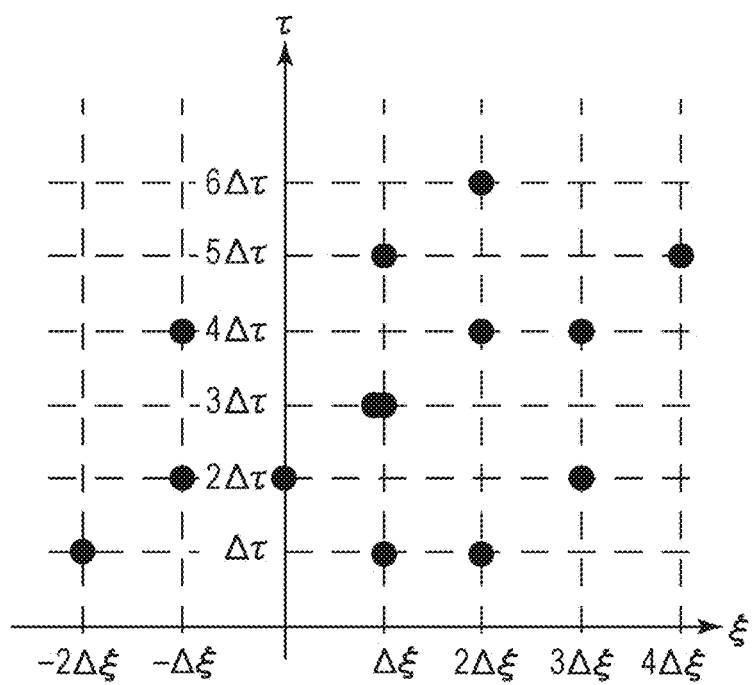
Figure 10:
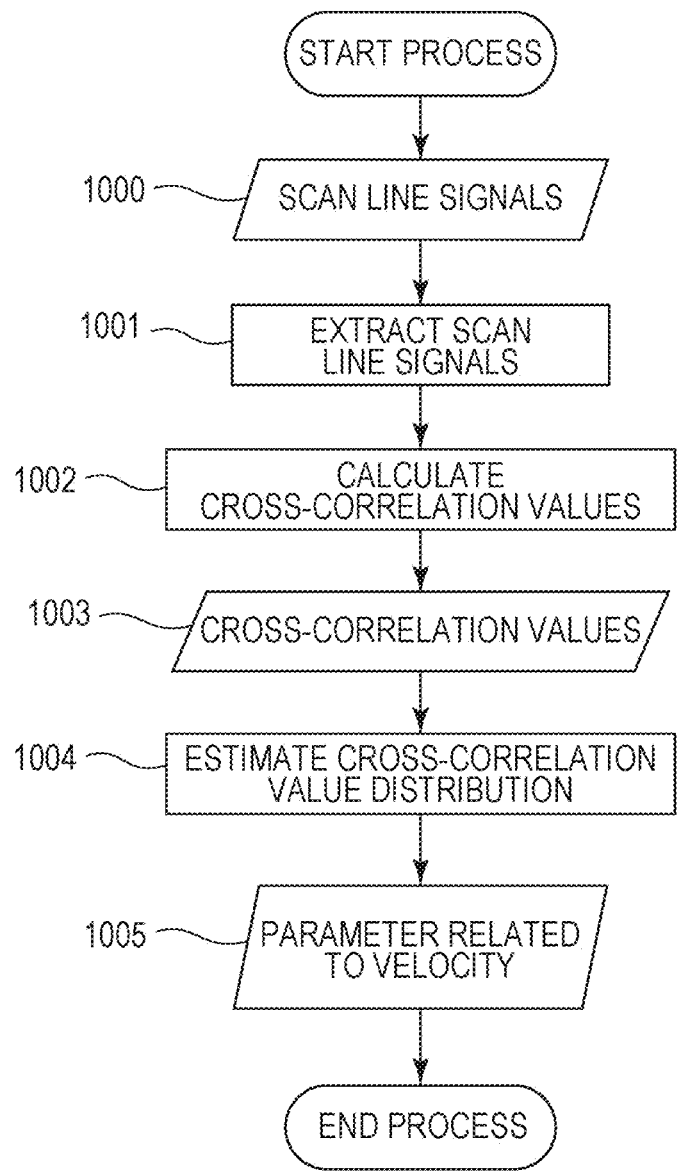
FIG. 10 is a flowchart showing processing steps according to the second embodiment.

A second embodiment of the present invention will be described with reference to FIGS. 1, 9, and 10. In the present embodiment, an example will be described in which the cross-correlation value is calculated by a combination of a plurality of random scan line signals and the velocity of the scatterer group is more accurately and stably obtained.

An apparatus configuration of the subject information acquisition apparatus of the present embodiment is the same as that described using FIG. 1, so that the description of the components will be omitted and only process content of the correlation calculation block 007 and the correlation pattern processing block 008, which is different from that described above, will be described. FIGS. 9A and 9B are diagrams for explaining the process of the correlation calculation block 007 and the correlation pattern processing block 008. FIG. 10 is a flowchart showing the process flow in the correlation calculation block 007 and the correlation pattern processing block 008.

In step 1000, scan line signals are inputted into the correlation calculation block 007 from the delay and sum block 006. The process described above is the same as that in the basic process flow and the process flow of the first embodiment.

In step 1001, the correlation calculation block 007 extracts scan line signals at positions of interest from a plurality of inputted scan line signals. FIG. 9A shows acquisition timing and acquisition positions of the scan line signals to be extracted at the positions of interest among the scan line signals inputted into the correlation calculation block 007. In FIG. 9A, the horizontal axis represents the acquisition position and the vertical axis represents the acquisition timing (acquisition time). For example, regarding the scan line signal indicated by a point f3, the acquisition position is $3\Delta\xi$ and the acquisition timing is $2\Delta\tau$.

In step 1002, the correlation calculation block 007 extracts two scan line signals from M types of scan line signals acquired in this way and calculates a cross-correlation value. M indicates a positive integer. Since the scan line signals are selected from the M types of scan line signals, it is possible to calculate $M \times (M-1)/2$ cross-correlation values.

In step 1003, the cross-correlation values outputted from the correlation calculation block 007 are inputted into the correlation pattern processing block 008.

In step 1004, the correlation pattern processing block 008 estimates a distribution of the cross-correlation values by using the plurality of inputted cross-correlation values. FIG. 9B shows a state in which the cross-correlation values are plotted, which can be calculated from the combination of the scan line signals that can be represented by the points f1 to f7 in FIG. 9A. Hereinafter, some examples will be described.

The cross-correlation value between the scan line signal that can be represented by the point f1 and the scan line signal that can be represented by the point f2 is plotted at a position of $\Delta\xi$ on the horizontal axis and $\Delta\tau$ on the vertical axis in FIG. 9B. The cross-correlation value between the scan line signal that can be represented by the point f1 and the scan line signal that can be represented by the point f3 is plotted at a position of $3\Delta\xi$ on the horizontal axis and $2\Delta\tau$ on the vertical axis in FIG. 9B. The cross-correlation value between the scan line signal that can be represented by the point f4 and the scan line signal that can be represented by the point f5 is plotted at a position of $\Delta\xi$ on the horizontal axis and $\Delta\tau$ on the vertical axis. The cross-correlation value between the scan line signal that can be represented by the point f1 and the scan line signal that can be represented by the point f2 and the cross-correlation value between the scan line signal that can be represented by the point f4 and the scan line signal that can be represented by the point f6 are plotted at the same position in FIG. 9B. In this way, by averaging the cross-correlation values plotted at the same position, it is possible to more stably calculate the cross-correlation value and further improve the accuracy of estimating the velocity. The distribution of the cross-correlation values is estimated by using the following formula which uses cross-correlation values at many points as input.

$$(\xi_A, \tau_A, v_A) = \arg\min_{\xi_0, \tau_0, v} \sum_{i=k}^{k+N} \alpha_i \{\rho_i - \rho'_i(\xi_0, \tau_0, v)\}^2 \quad \text{[Formula 2]}$$

Here, $\rho i$ represents the cross-correlation value at a position of the distance difference $\xi i$ and the time difference $\tau i$ and $\rho i'(\xi 0, \tau 0, v)$ represents a theoretical value of the cross-correlation value at the distance difference $\xi 0$, the time difference $\tau 0$, and the velocity v. N is the number of combinations of the cross-correlation values (the number of types of plotted positions) used to estimate the distribution of the cross-correlation values. For example, N=13 in FIG. 9B. In the formula 2, $\alpha i$ is a weight, and for example, $\alpha i$ can be set so that $\alpha i = di$ or $\alpha i = \rho i \times di$ by using di that can be obtained by the formula 3.

$$d_i = \sqrt{(\xi_i/\xi_0)^2 + (\tau_i/\tau_0)^2} \quad \text{[Formula 3]}$$

It is assumed that the farther from the origin on the plane represented by two axes including the axis of time difference and the axis of distance difference, the higher the accuracy of estimation of the elliptical shape, and the higher the cross-correlation value, the higher the reliability, so that it can be expected that the estimation accuracy of the elliptical shape is further improved by using the weight $\alpha i$. Here, the theoretical value can be calculated by assuming that the contour line of the cross-correlation value on the plane represented by two axes including the axis of time difference and the axis of distance difference can be approximated by the elliptical shape.

Further, $\alpha i$ may be set to the number of the cross-correlation values plotted at the same position or a coefficient reflecting the number (a coefficient that increases as the number increases). When setting $\alpha i$ in this way, it is possible to estimate the distribution by weighting each cross-correlation value whose accuracy is improved by averaging the cross-correlation values, so that the estimation accuracy of the elliptical shape is further improved.

As described above, also in the present embodiment, the distribution of the cross-correlation values on the plane represented by two axes including the axis of time difference and the axis of distance difference is acquired, so that information related to the maximum value of the cross-correlation values at a certain time difference can be obtained, and thus more accurate moving information can be obtained. In step 1005, the correlation pattern processing block 008 outputs a parameter related the velocity obtained by the steps described above to the image processing block 010 as the moving information. The subsequent process of the image processing block 010 is the same as that in the first embodiment, so that the description will be omitted.

Figure 12A:
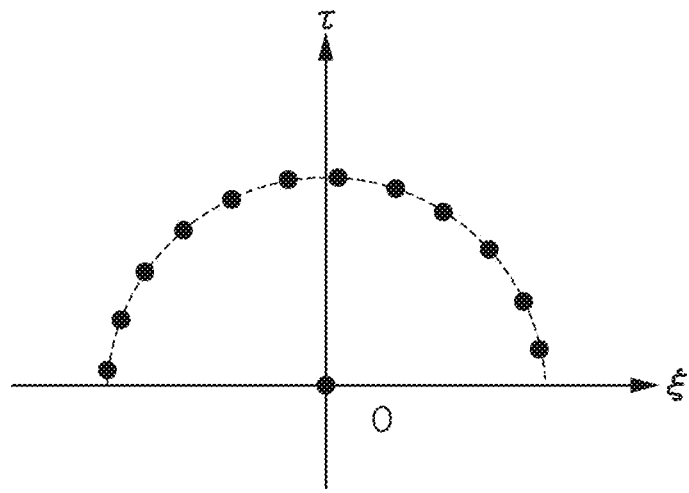
FIGS. 12A and 12B are diagrams for explaining a concept of a process for acquiring a velocity distribution.
Figure 12B:
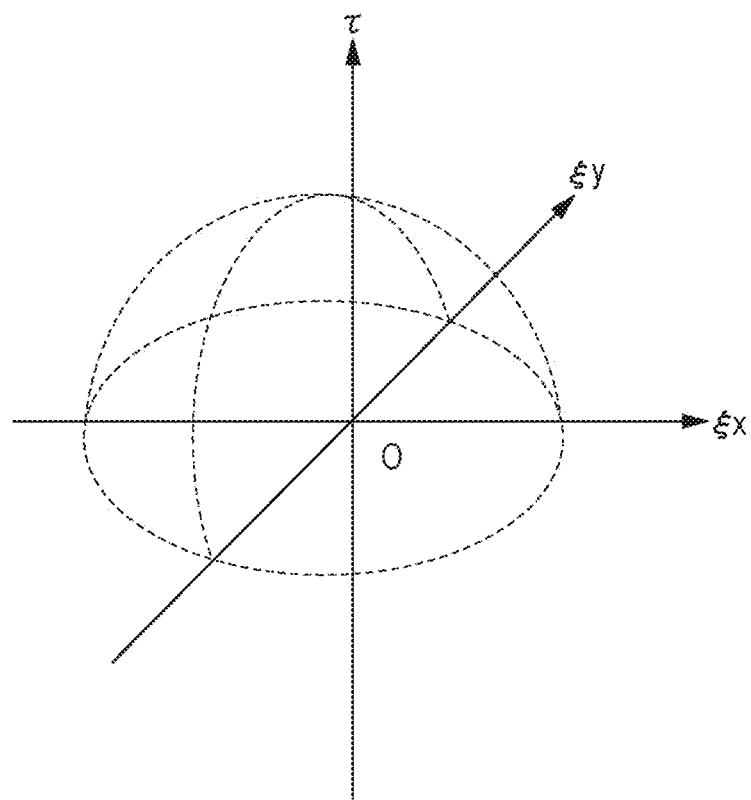

As shown in FIG. 12A, on the plane represented by two axes including the axis of time difference and the axis of distance difference, the velocity can be stably calculated regardless of the traveling direction of the scatterer group by calculating cross-correlation values at positions located in a plurality of directions with respect to the origin (for example, positions indicated by black dots in FIG. 12A). Further, as shown in FIG. 12B, in a space represented by three axes including the axis of time difference, the axis of a distance difference $\xi x$ in the x direction, and the axis of a distance difference $\xi y$ in the y direction perpendicular to the x direction, the moving information of the scatterer group can be acquired in a two-dimensional plane by calculating cross-correlation values at positions located in a plurality of directions with respect to the origin, such as, for example, at a plurality of points (not shown in FIG. 12B) on the hemisphere face indicated by dotted lines.

In the present embodiment, it is possible to calculate a larger number of cross-correlation values by combining a plurality of scan line signals, so that the temporal change of the scatterer group can be considered more accurately and the velocity can be stably and accurately obtained. In addition, the stability can be further improved by not using cross-correlation values using signals with a low S/N ratio and cross-correlation values having a small value for the correlation pattern processing block 008 to estimate the distribution of the cross-correlation values.

Moreover, it is possible to perform more accurate calculations of the cross-correlation value and the velocity by using a large number of scan line signals on scan lines (for example, three scan lines or five scan lines) near a region where the velocity is desired to be obtained. Theoretically, in a distribution of cross-correlation values on a coordinate space where the horizontal axis represents a distance difference between positions of interest and the vertical axis represents an acquisition time difference of scan line signals, when a cross-correlation value is partially differentiated by a velocity, a cross-correlation value in a region (coordinate point group) where the partially differentiated value is greater than that in the other regions (coordinate point groups) is used, so that an accurate velocity calculation can be performed. In a region where the distance difference between the points of interest is small, a region including a large partially differentiated value often appears. Therefore, it is desired to use scan line signals obtained at neighboring positions in a region to be observed. In particular, it is preferable to use scan line signals at three points on three scan lines adjacent to each other. To use a larger number of scan lines near the region where the velocity is desired to be obtained, a method can be used in which the aforementioned weight is increased with respect to the cross-correlation value obtained by the combination of the scan line signals or the number of transmission/reception operations per unit time is increased compared with that in other regions.

Third Embodiment

Next, a third embodiment will be described. The present embodiment calculates the cross-correlation value in only a region containing blood. FIG. 11 shows a system schematic diagram of a subject information acquisition apparatus according to the present embodiment. An apparatus configuration of the subject information acquisition apparatus of the present embodiment is basically the same as that shown in FIG. 1 except that a blood flow position extraction block 012 is added to the apparatus configuration of FIG. 1, so that portions different from those in the embodiments described above will be described.

In the present embodiment, scan line signals are outputted from the delay and sum block 006 to the image generation block 009, the correlation calculation block 007, and the blood flow position extraction block 012. The process after the scan line signals are inputted into the image generation block 009 is the same as that in the embodiments described above, so that the description thereof will be omitted.

The blood flow position extraction block 012 performs power Doppler processing by using a plurality of scan line signals inputted from the delay and sum block 006. The power Doppler processing is processing for specifying a target range that contains blood in the subject (that is, an object such as scatters including a plurality of red blood cells). In other words, the blood flow position extraction block 012 is a target range specification unit in the present invention.

However, in the present invention, the method for specifying the target range containing the object is not limited to the power Doppler processing, but color Doppler processing may also be used. Also, a method may be used which extracts a target range such as a blood vessel on the basis of normal impedance intensity data (intensity data of a distribution reflecting differences between acoustic impedances in the subject, such as a normal B-mode image). In this case, for example, in the same manner as the image generation block 009, a plurality of envelope curve signals are calculated on the basis of a plurality of scan line signals and the impedance intensity data is acquired by using the envelope curve signals. Then, a blood vessel wall is extracted by extracting positions where the intensity is greater than a predetermined value from the distribution of the impedance intensity data, so that the range of the vessel can be acquired as the target range. Further, an image of the impedance intensity data may be displayed on the image display system 011 and a range specified by a user may be acquired as the target range.

In the present embodiment, the blood flow position extraction block 012, which is a target range specification unit, outputs information of the target range containing a blood flow extracted by the power Doppler processing to the system control unit 004.

The correlation calculation block 007 calculates the cross-correlation value by using only the scan line signals in the target range containing the blood flow among the scan line signals inputted from the delay and sum block 006 according to the information of the target range containing the blood flow inputted from the system control unit 004. The process after that is the same as that in the basic process flow and the first and the second embodiments.

According to the present embodiment, the cross-correlation values are calculated in only the target range containing a blood flow, so that the calculation load is small, and thus it is possible to provide a much smaller apparatus.

Fourth Embodiment

The present embodiment acquires scan line signals at a plurality of positions at the same time and uses the scan line signals. A configuration of the subject information acquisition apparatus of the present embodiment is basically the same as that described using FIGS. 1 and 11, so that only functional units different from those described using FIGS. 1 and 11 will be described.

In the present embodiment, a process in which elastic waves are transmitted in a plurality of directions or to a plurality of positions at the same time and the reflected waves of the elastic waves are received is performed a plurality of times. In the present invention, an operation to transmit the elastic waves "at the same time" includes not only a case in which the elastic waves are transmitted at exactly the same time, but also a case in which the elastic waves are not transmitted at exactly the same time but reception signals can be handled as if the elastic waves were transmitted at the same time.

The delay and sum block 006 performs the delay and sum process by using reception signals and calculates a plurality of scan line signals. The correlation calculation block 007 calculates a plurality of cross-correlation values between scan line signals at a plurality of different positions for elastic waves transmitted at different times (that is, based on reflected waves based on elastic waves transmitted at different transmission times).

The correlation pattern processing block 008 determines whether or not there is a peak in the plurality of cross-correlation values, and when there is a peak, the correlation pattern processing block 008 estimates a position where the cross-correlation value is the peak. Then, the correlation pattern processing block 008 calculates moving information on the basis of the time difference and the distance difference where the cross-correlation value is the peak. When there is no peak in the plurality of cross-correlation values, the correlation pattern processing block 008 calculates the moving information by using one of methods in the embodiments described above. Even when there is a peak in the plurality of cross-correlation values, the correlation pattern processing block 008 can calculate the moving information by using one of methods in the embodiments described above. The present embodiment can also be implemented by transmitting elastic waves to a certain region, the delay and sum process is performed related to a plurality of directions or positions in the region where the elastic waves are transmitted, and calculating a plurality of scan line signals.

In the present embodiment, the moving information can be obtained by switching a case in which the distribution of the cross-correlation values on the plane represented by two axes including the axis of time difference and the axis of distance difference is acquired as in the embodiments described above and a case in which the peak of the cross-correlation values is used.

Fifth Embodiment

The present invention can be realized by executing the process described below. Software (program) that realizes functions of the embodiments described above is supplied to a system or an apparatus through a network or various storage media and a computer (or CPU or MPU) of the system or the apparatus reads the program and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-243607, filed Nov. 7, 2011, and Japanese Patent Application No. 2012-023343, filed Feb. 6, 2012, which are hereby incorporated by reference herein in their entirety.

REFERENCE SIGNS LIST

000 subject
001 probe
002 conversion element
003 transmission circuit system
004 system control unit
005 reception circuit system
006 delay and sum block
007 correlation calculation block
008 correlation pattern processing block
009 image generation block
010 image processing block
011 image display system
012 blood flow position extraction block
301 blood vessel
302 scatterer group
303, 304 scan line
601 to 606 scan line

The invention claimed is:

1. A subject information acquisition apparatus comprising:
    a scan line signal acquiring processor that acquires a plurality of scan line signals each indicative of a reflected wave from each of a plurality of positions along a scan line in the subject by using a plurality of reception signals outputted from a plurality of transducers that transmits elastic waves to the subject and receives the reflected wave reflected in the subject; and
    a processor that acquires moving information indicative of motion of an object in the subject by using the plurality of scan line signals, wherein the moving information comprises at least one of a velocity of the object, a velocity distribution, a displacement of the object and a displacement distribution,
    wherein the processor acquires the moving information, on the basis of a shape formed by a contour line of cross-correlation values on a plane represented by an axis of time difference and an axis of distance difference, the cross-correlation values being cross-correlation values between scan line signals at different positions in the subject, and
    wherein the processor controls a display device to display a graphical representation of the moving information indicative of the motion of an object in the subject.

2. The subject information acquisition apparatus according to claim 1, wherein the processor
    acquires the shape formed by the contour line of the cross-correlation values as a shape approximated to an ellipse, and
    acquires, as the moving information, a reciprocal of a slope of a line connecting a point where a cross-correlation values on the shape is maximum at a certain time difference in a direction of the axis of time difference and the origin thereof.

3. The subject information acquisition apparatus according to claim 1, wherein the processor acquires the moving information by further using a cross-correlation value between scan line signals at a same position of the plane.

4. The subject information acquisition apparatus according to claim 1, wherein the plurality of transducers perform electronic scanning, in which a beam of the elastic wave is sequentially transmitted to the plurality of positions in the subject, twice or more, the scan line signal acquiring processor acquires the plurality of scan line signals by performing the electronic scanning twice or more, and the processor acquires a distribution of the cross-correlation values by using cross-correlation values between scan line signals acquired by a second and following electronic scanning and a scan line signal at a datum point acquired by a first electronic scanning, and cross-correlation values between the scan line signal at the datum point acquired by the first electronic scanning and scan line signals other than the scan line signal acquired by the first electronic scanning.

5. The subject information acquisition apparatus according to claim 1, wherein the processor acquires a distribution of the cross-correlation values by using cross-correlation values between scan line signals that are randomly combined.

6. The subject information acquisition apparatus according to claim 1, further comprising:

a target range specifying processor that specifies a target range where the moving information of the object is acquired, wherein the moving information in the target range is acquired by using only scan line signals in the target range specified by the target range specifying processor.

7. The subject information acquisition apparatus according to claim 1, wherein, the processor acquires a velocity distribution of the object as the moving information.

8. The subject information acquisition apparatus according to claim 1, further comprising the plurality of transducers.

9. The subject information acquisition apparatus according to claim 1, wherein the processor controls the display device to display the graphical representation of the moving information as an image.

10. The subject information acquisition apparatus according to claim 9, wherein the graphical representation of the moving information is superimposed or arranged side by side with data of impedance intensity of the subject.

11. The subject information acquisition apparatus according to claim 9, wherein the information indicative of the moving information includes at least one of velocity distribution, direction of velocity, and magnitude of velocity.

12. A non-transitory computer-readable storage medium storing a program for causing a computer to execute steps, comprising:

a step of receiving a plurality of reception signals outputted from a plurality of transducers by transmitting an elastic wave to the subject and receiving a reflected wave that is reflected at a plurality of positions in the subject;

a step of acquiring a plurality of scan line signals each indicative of a reflected wave from each of the plurality of positions along a scan line in the subject by using the plurality of reception signals; and a step of acquiring moving information indicative of motion of an object in the subject by using the plurality of scan line signals, wherein the moving information comprises at least one of a velocity of the object, a velocity distribution, a displacement of the object and a displacement distribution, wherein, in the step of acquiring the moving information, the moving information of the object is acquired on the basis of a shape formed by a contour line of cross-correlation values on a plane represented by an axis of time difference and an axis of distance difference, the cross-correlation values being cross-correlation values between scan line signals at different positions in the subject, and a step of causing a display device to display a graphical representation of the moving information indicative of the motion of an object in the subject.

13. The non-transitory computer-readable storage medium according to claim 12, wherein the program further causes the computer to execute a step of acquiring the shape formed by the contour line of the cross-correlation values as a shape approximated to an ellipse, and a step of acquiring, as the moving information, a reciprocal of a slope of a line connecting a point where a cross-correlation values on the shape is maximum at a certain time difference in a direction of the axis of time difference and the origin thereof.

14. The non-transitory computer-readable storage medium according to claim 12, wherein the program further causes the computer to execute a step of acquiring the moving information by further using a cross-correlation value between scan line signals at a same position of the plane.

15. The non-transitory computer-readable storage medium according to claim 12, wherein the program further causes the computer to execute a step of acquiring the plurality of scan line signals by performing the electronic scanning twice or more, and a step of acquiring a distribution of the cross-correlation values by using cross-correlation values between scan line signals acquired by a second and following electronic scanning and a scan line signal at a datum point acquired by a first electronic scanning, and cross-correlation values between the scan line signal at the datum point acquired by the first electronic scanning and scan line signals other than the scan line signal acquired by the first electronic scanning.

16. The non-transitory computer-readable storage medium according to claim 12, wherein the program further causes the computer to execute a step of acquiring a distribution of the cross-correlation values by using cross-correlation values between scan line signals that are randomly combined.

17. The non-transitory computer-readable storage medium according to claim 12, wherein the program further causes the computer to execute a step of specifying a target range where the moving information of the object is acquired, wherein the moving information in the target range is acquired by using only scan line signals in the target range specified by the step of specifying.

18. The non-transitory computer-readable storage medium according g to claim 12, wherein the program further causes the computer to execute a step of acquiring a velocity distribution of the object as the moving information.

19. The non-transitory computer-readable storage medium according to claim 12, wherein the step of causing includes controlling the display device to display the graphical representation of the moving information as an image.

20. The non-transitory computer-readable storage medium according to claim 19, wherein the graphical representation of the moving information is superimposed or arranged side by side with data of impedance intensity of the subject.

21. The non-transitory computer-readable storage medium according to claim 19, wherein the information indicative of the moving information includes at least one of velocity distribution, direction of velocity, and magnitude of velocity.

\* \* \* \* \*